(12) United States Patent
Glickman et al.

(10) Patent No.: US 6,806,056 B2
(45) Date of Patent: Oct. 19, 2004

(54) FLUORESCENT CAPTURE ASSAY FOR KINASE ACTIVITY EMPLOYING AN ANTI-PHOSPHOTYROSINE ANTIBODY AS BOTH THE CAPTURE AGENT AND DETECTING AGENT

(75) Inventors: J. Fraser Glickman, Basel (CH); James Inglese, Lansdale, PA (US); Bassam Damaj, San Diego, CA (US); Maria L. Webb, Flemington, NJ (US); Jonathan J. Burbaum, San Diego, CA (US)

(73) Assignee: Pharmacopeia Drug Discovery, Inc., Cranbury, NJ (US)

( * ) Notice: Subject to any disclaimer, the term of this patent is extended or adjusted under 35 U.S.C. 154(b) by 90 days.

(21) Appl. No.: 10/125,784

(22) Filed: Apr. 18, 2002

(65) Prior Publication Data

US 2002/0177179 A1 Nov. 28, 2002

Related U.S. Application Data

(63) Continuation of application No. PCT/US00/29284, filed on Oct. 23, 2000, which is a continuation of application No. 09/425,549, filed on Oct. 22, 1999, now Pat. No. 6,406,869.

(51) Int. Cl.[7] .................. G01N 33/567; G01N 33/566
(52) U.S. Cl. .............. 435/7.21; 435/7.1; 435/7.23; 435/7.4; 435/7.94; 435/21; 424/9.1; 436/501; 436/518; 436/543; 436/547; 436/548
(58) Field of Search ............................ 435/4, 5, 6, 7.1, 435/7.21, 7.23, 7.24, 7.4, 7.94, 15, 21, 29, 188, 792; 424/9.1; 436/501, 518, 543, 547, 548

(56) References Cited

U.S. PATENT DOCUMENTS

| | | | |
|---|---|---|---|
| 5,599,681 A | 2/1997 | Epstein et al. ............. 435/7.23 |
| 5,616,726 A | 4/1997 | Mitsuda et al. ............. 548/475 |
| 5,759,787 A | 6/1998 | Strulovici .................... 435/7.4 |
| 5,763,198 A | * 6/1998 | Hirth et al. ................. 435/7.21 |
| 5,958,719 A | 9/1999 | Ullrich et al. ................ 435/21 |
| 6,066,462 A | 5/2000 | Goueli ........................ 435/7.1 |

FOREIGN PATENT DOCUMENTS

| | | | | |
|---|---|---|---|---|
| EP | 0 730 740 B1 | 2/1998 | | |
| WO | WO 95/04136 | 2/1995 | | |
| WO | WO-95/04136 A1 | * 2/1995 | ............ C12N/9/12 |
| WO | WO-96/40276 A1 | * 12/1996 | .......... A61K/49/00 |
| WO | WO-99/29894 A1 | * 6/1999 | ............ C12Q/1/48 |

OTHER PUBLICATIONS

Park et al. Homogeneous proximity tyrosine kinase assays. Analytical Biochemistry, vol. 269, pp. 94–104, Apr. 1999.*

Cleaveland et al. "A Microtiter–Based Assay for the Detection of Protein Tyrosine Kinase Activity" *Analytical Biochemstry 190*, 249–253 (1990).

Giorgetti et al. "Insulin stimulates phosphatidylinositol–3–kinase activity in rat adipocytes" *Eur. J. Biochem. 207,* 599–606 (1992).

* cited by examiner

*Primary Examiner*—Long V. Le
*Assistant Examiner*—Lisa V Cook
(74) *Attorney, Agent, or Firm*—Heslin Rothenberg Farley & Mesiti P.C.; Kathy Smith Dias, Esq.

(57) ABSTRACT

A method for determining the level of tyrosine kinase activity in a biological sample is disclosed. The method employs an anti-phosphotyrosine antibody as both the capture agent and the detecting agent. The detecting antibody is labeled with a fluorescent label, for instance, Cy5, Cy5.5 or Cy7 or a lanthanide ion, such as europium, as the signal generating entity. The method is particularly well suited to high throughput screening, for example, for compounds which modulate tyrosine kinase activity.

9 Claims, 2 Drawing Sheets fig. 1 fig. 2

US 6,806,056 B2

FLUORESCENT CAPTURE ASSAY FOR KINASE ACTIVITY EMPLOYING AN ANTI-PHOSPHOTYROSINE ANTIBODY AS BOTH THE CAPTURE AGENT AND DETECTING AGENT

CROSS REFERENCE TO RELATED APPLICATIONS

This application is a continuation of PCT/US00/29284 filed Oct. 23, 2000 which is a continuation from U.S. application Ser. No. 09/425,549 filed Oct. 22, 1999, now issued as U.S. Pat. No. 6,406,869 the entire disclosures of which are incorporated herein by reference.

FIELD OF THE INVENTION

The present invention relates to a method for determining the level of kinase activity in a biological sample and, in particular, to a method of identifying drugs that inhibit tyrosine kinases, or drugs that inhibit receptors associated with tyrosine kinases.

BACKGROUND OF THE INVENTION

Protein phosphorylation is a common regulatory mechanism used by cells to selectively modify proteins carrying regulatory signals from outside the cell to the nucleus. The proteins that execute these biochemical modifications are a group of enzymes known as protein kinases. They may further be defined by the substrate residue that they target for phosphorylation. One group of protein kinases are the tyrosine kinases (TK's), which selectively phosphorylate a target protein on its tyrosine residues. Some tyrosine kinases are membrane-bound receptors and upon activation by a ligand, can autophosphorylate as well as modify substrates. The initiation of sequential phosphorylation by ligand stimulation is a paradigm that underlies the action of such effectors as, for example, epidermal growth factor (EGF), insulin, platelet-derived growth factor (PDGF), and fibroblast growth factor (FGF). The receptors for these ligands are tyrosine kinases and provide the interface between the binding of a ligand (hormone, growth factor) to the activation of one or more biochemical pathways. Ligand binding to a receptor tyrosine kinase activates its intrinsic enzymatic activity. Tyrosine kinases can also be cytoplasmic, non-receptor type enzymes and act as a downstream component of a signal transduction pathway.

The profound cellular effects mediated by tyrosine kinases, for example, their putative role in angiogenesis [Giroux, S. et al. Curr. Biol. 9: 369 (1999)] and lymphoid development [Nosaka, T., et al. Science 270: 800, (1995)] coupled with the implication that mutant or defective tyrosine kinase variants may be involved in tumorigenesis [Jeffers, M., et al. PNAS 94: 11445, (1997)], have made them attractive targets for the development of new therapeutic molecules.

Traditional methods for measuring the phosphorylation state of cellular proteins have relied on $^{32}$P-orthophosphate incorporation, for example, by exposing cells cultured in the presence of $^{32}$P-orthophosphate to the appropriate ligand or activator. Alternatively, phosphorylated tyrosine residues can be detected in immunoassays, for example, immunoprecipitation or blotting using a radiolabeled anti-phosphotyrosine antibody. The fact that the techniques for detecting radioactive isotope (i.e. blotting, immunoprecipitation, gel electrophoresis) are very time consuming, however, minimizes the appeal of these methodologies for high throughput screening.

More recent methods utilize a standard enzyme-linked immunosorbent assay (ELISA) for measuring kinase activity. These methods utilize purified heterologous substrate protein or synthetic substrate peptides anchored to a microtiter plate. After exposure of the substrate molecule to a sample containing the appropriate kinase, the level of phosphorylation is evaluated with anti-phosphotyrosine antibodies to quantitate the amount of phosphorylated protein bound to the plate. The obvious limitation of this type of assay is that the activity of a kinase specific for the particular substrate used, is the only activity detected. Additionally, methods such as protein tyrosine kinase enzyme assays are unable to eliminate as potential drug candidates, inhibitors which are not cell permeable and, therefore, are not good choices for therapeutic agents.

Hirth et al., U.S. Pat. No. 5,763,198, for example, describes an ELISA-type assay in which a substrate-specific antibody is used as an anchoring molecule to isolate a protein substrate from a cell lysate preparation and immobilize it on a solid phase support. Hirth's method then determines the level of kinase activity by evaluating the tyrosine phosphorylation state of the protein substrate bound to the solid phase using an anti-phosphotyrosine antibody as the detecting molecule. Other methods for measuring tyrosine kinase activity, particularly tyrosine kinase receptor activity, are described in WO95/04136, EP 0 730 740 B1, and U.S. Pat. No. 5,599,681.

The availability of an efficient, high throughput assay of kinase activity, particularly, one that is cell-based, is highly desirable because it provides the means, not only to characterize the phosphorylation status of a cell, but to identify agonists and antagonists useful as therapeutic agents for the treatment of a wide variety of human diseases.

SUMMARY OF THE INVENTION

Because the method of the present invention uses a capture agent capable of capturing any molecule containing a phosphorylated tyrosine, it can bind any tyrosine kinase substrate which has been phosphorylated. The method is, therefore, not limited to the measurement of a single tyrosine kinase. The method can be used with any kinase molecule without the necessity of having to use different capture agents for different kinases. Furthermore, the method of the present invention has the advantage of detecting cellular signaling events downstream of the receptor, thereby providing a means for detecting in a single test a drug's ability to inhibit more than one therapeutic target.

In one aspect, the invention relates to a method for measuring tyrosine kinase activity in a biological sample by contacting the sample with a solid phase coated with a first anti-phosphotyrosine antibody to capture phosphorylated proteins contained in the biological sample, and determining the amount of phosphorylated protein captured using a second labeled anti-phosphotyrosine antibody as the detecting molecule. The biological sample may be a purified homogeneous tyrosine kinase, a cell fraction, such as a cytosol or cell membrane preparation, cell or tissue extracts or bodily fluids, such as serum, plasma, urine or the like.

In another aspect, the invention relates to a method for measuring tyrosine kinase activity in a biological sample which employs a lanthanide ion as the reporter group on the labeled detecting antibody. By virtue of their unique fluorescence properties, use of lanthanide ions such as samarium (Sm), dysprosium (Dy), europium (Eu) and terbium (Tb) as labels make the method of the invention particularly well suited for high throughput screening.

In yet another aspect, the invention features a method of screening for molecules, including agonist/antagonist small molecules, that modulate tyrosine kinase activity in whole cells, cell fractions, purified tyrosine kinase preparations or biological fluids. Samples are incubated with potential agonists or antagonists, and assayed for tyrosine kinase activity in accordance with the method described herein. Where the biological sample is a preparation of whole cells, the cells are fractionated, and the cytosol or cell membrane fractions are assayed for tyrosine kinase activity in accordance with the method of the present invention. The method can be used to evaluate cell activation through a general mechanism or through specific receptor activation by directly measuring the level of phosphorylated proteins within a biological sample that results from cell activation.

In yet another aspect, the invention relates to a kit for use in measuring the level of tyrosine kinase activity in a biological sample. The kit provides a solid support, for example a microtiter plate or beads, which is coated with an anti-phosphotyrosine antibody which captures phosphorylated proteins contained within the sample. A labeled anti-phosphotyrosine antibody is also provided to detect the amount of phosphorylated protein bound to the solid phase.

DETAILED DESCRIPTION OF THE INVENTION

All patents, applications, publications, or other references that are listed herein are hereby incorporated by reference.

In the description that follows, certain conventions will be followed as regards the usage of terminology: The term "solid phase" refers to the solid support to which a capture agent, for example, an antibody, is attached and, in one embodiment, may be a microtiter plate. The method can be carried out in conventional 96-well microtiter plates, or in any other container or on any surface capable of holding liquid samples and of being scanned by the appropriate detection device, for example a plate reader or microscope. Other examples include 6 to 1536-well plates, and microscope slides.

In another embodiment, a suspendable solid phase can be employed, including cellulose beads, controlled pore-glass beads, silica gels, polyacrylamide beads, latex beads, dimethylacrylamide beads, glass particles coated with hydrophobic polymers and other types of polystyrene beads. The preferred bead size is less than about 50 μm in diameter, most preferably less than 10 μm but greater than 1 μm. A preferred suspendable support is a 6.2 μm bead made of polystyrene and commercially available from Spherotech (Libertyville, Ill.). Such beads are avidin coated or coated with protein A, typically containing $10^6$ binding sites per bead.

The term "capture agent" refers to a compound or agent which is able to adhere to a solid phase and which is selective for phosphorylated proteins contained in the biological sample to be assayed and typically is an affinity-purified polyclonal antibody or a monoclonal antibody.

Solid phases used for the immobilization of phosphorylated molecules may be prepared by coating with the capture agent (anti-phosphotyrosine), either directly or indirectly. Methods for immobilizing antibodies are known in the art and are described in Harlow, E. and D. Lane, *Antibodies: A Laboratory Manual*, (1988) Cold Spring Harbor Laboratory, Cold Spring Harbor, N.Y. which is incorporated herein by reference. In one embodiment, the anti-phosphotyrosine antibody is immobilized to the solid phase by an antibody bound to the solid phase which is specific for the Fc portion of the anti-phosphotyrosine antibody. In another embodiment, the anti-phosphotyrosine antibody is adsorbed directly to the solid phase.

The term "biological sample" refers to any source of protein tyrosine kinase activity and is intended to encompass purified kinase preparations, cells, both whole and fractionated, cell and tissue extracts, and bodily fluids, for example, urine, serum, plasma and the like.

Sandwich assays are among the most useful and commonly used assays and are particularly useful in the present invention. A number of variations of the sandwich assay technique exist. In a typical assay, an antibody is brought into contact with a biological sample containing one or more proteins of interest. After a suitable period of incubation, for a period of time sufficient to allow formation of an antibody-protein complex, a second antibody, labelled with a reporter molecule capable of producing a detectable signal, is then added and incubated allowing sufficient time for the formation of a tertiary complex. The presence of the second antibody bound is determined by observation of the visible signal, and may be quantitated by comparing with a control sample containing known amounts of hapten. Variations on the assay include using a first antibody labelled with a reporter molecule. In addition, the "capture" antibodies may be immobilized on a solid support.

Typically, the capture agent and the detecting agent are different molecules each having specificity for different regions of the molecule to be captured. Capture agents are usually chosen so that binding of the capture agent does not sterically block access to the phosphorylated tyrosines of the molecule of interest. It has now been unexpectedly found that an anti-phosphotyrosine antibody can be used as the capture agent and as the detection agent in the same assay. The method of the instant invention employs a standard ELISA-like sandwich assay. Unlike other similar assays, however, its versatility stems from its use of an anti-phosphotyrosine antibody as both the capture agent and the detection agent. By doing so, the method is able to capture any tyrosine-containing protein in the biological sample which is phosphorylated, thereby providing a mechanism to evaluate phosphorylation that results from cell activation.

Activation of a cell most frequently occurs when an appropriate ligand binds to its receptor on the cell surface. Such ligands may include growth and differentiation factors such as epidermal growth factor (EGF); platelet-derived growth factor (PDGF); chemokines, such as the interleukins; SDF-1 and GM-CSF (activates JAK2 in a variety of cells). Cells can also be activated by mitogen stimulation, for example, concanavalin A or phytohemagglutanin for T-cells, pokeweed mitogen or lipopolysaccharide for B-cells; or an antibody to a cell surface marker, such as IgM.

Because they focus on a specific substrate, current methodologies are only able to detect phosphorylation by a particular kinase. The method of the present invention confers an advantage in that it utilizes a capture agent which can capture any protein in the biological sample such as a cell lysate which has a tyrosine residue that is phosphorylated. Because detection is not limited to a single kinase, a broader perspective of the overall phosphorylation resulting from an activation event can be obtained. Furthermore, identification of inhibitors which down-regulate ligand-induced phosphorylation is possible.

In one embodiment, the method of detection for the subject method is time resolved fluorescence and the detecting agent, anti-phosphotyrosine antibody, is labeled with a lanthanide ion, preferably, europium. Lanthanide ions have unique fluorescence properties which make them particularly well suited for high throughput assays such as the method described herein. While samarium (Sm) and dysprosium (Dy) are suitable for use in the instant method, europium (Eu) and terbium (Tb) are preferred, with europium being most preferred.

In another embodiment, microscopy, more preferably confocal microscopy is useful for determining the amount of labeled anti-phosphotyrosine antibody bound to the molecules captured on the antibody coated solid support. In this embodiment, as discussed in more detail below, fluorescent labels such as cyanine dyes Cy-5, Cy5.5 and Cy7 are employed.

In accordance with one embodiment of the method of the present invention, a solid support, for example, a 96-well polystyrene microtiter plate is coated with an anti-phosphotyrosine antibody, for example, pY99 (Santa Cruz Biotech, Inc., Santa Cruz, Calif.), by preparing a solution having an antibody concentration in the range of 0.01 µg/ml to 25 µg/ml, with a preferred concentration of 2.5 µg/ml, in Tris buffered saline (TBS) having a pH in the range of 7.5–8.5 and adding an aliquot of antibody solution to each well of the plate. A variety of anti-phosphotyrosine antibodies, available commercially from a number of sources, are suitable for the method of the present invention. For example, PY-7E1, PY-1B2, and PY20 are monoclonal mouse anti-phosphotyrosine antibodies available from Zymed (San Francisco, Calif.) individually or as a cocktail sold under the trademark PY-PLUS™. Zymed also offers an affinity-purified polyclonal rabbit anti-phosphotyrosine antibody, Z-PY1. A mouse anti-phosphotyrosine antibody, clone PT-66 is available from Sigma (St. Louis, Mo.). Furthermore, polyclonal phosphotyrosine antibodies may be raised in a variety of species according to immunization methods well known in the art. A method for the production of monoclonal phosphotyrosine antibodies is described in U.S. Pat. No. 4,543,439, which is incorporated herein by reference.

The plate is then incubated for a period of time sufficient to allow adsorption of the antibody to the plate. Plates coated in this manner are then rinsed to remove excess antibody and a blocking solution, for example, that sold under the trademark, SUPERBLOCK® (Pierce Chemical, Rockford, Ill.) is added followed by an incubation period sufficient to allow any regions of the plate not coated with antibody to be coated with the blocking agent. Other suitable blocking agents include proteins that do not cross-react with any of the reagents in the assay, for example, bovine serum albumin (BSA), gelatin, casein or milk protein. At this point, the plates may be stored at 4° C. for up to two weeks.

An aliquot of the biological sample to be evaluated is added to the capture assay plate. Where the biological sample is a preparation of whole cells, prior to assay, the cells to be evaluated are lysed with 50 µl of a standard detergent buffer containing phosphatase inhibitors, for example, TRITON® X-100, 50 mM sodium fluoride, 2 mM EDTA, 2 mM EGTA. The plate containing the cell lysates is frozen at −80° C. and may be stored indefinitely. To assay the cell lysates for kinase activity, the plate is thawed at 37° C., and 100 µl of tris buffered saline with 0.1% TWEEN® 20 is added to each well. After shaking the plate for 15 minutes, 180 µl of the cell lysate from each well is transferred to the capture assay plate described above.

After addition of the sample, the assay plate is incubated at room temperature with shaking for a period of time sufficient to allow the phosphorylated proteins contained in the sample to bind to the antibody coated plate, for example, anywhere from 15 minutes to several hours. The plate is then washed to remove unbound protein. Relative phosphorylated protein levels are detected using a lanthanide-chelate labeled anti-phosphotyrosine antibody in tris buffered saline (pH 8.0). An anti-phosphotyrosine antibody which is different from or the same as the one used for the capture antibody may be labelled for use as the detecting molecule. Any of the anti-phosphotyrosine antibodies described above for use as the capture agent are suitable for use as the detecting antibody as well. Polyclonal, as well as monoclonal antibodies, may be labelled with a lanthanide ion.

In this embodiment, where time-resolved fluorescence is the detection method used, the method of the present invention employs a lanthanide-chelate as the label for the detecting antibody. The long-lived and sharp emission spectrum of certain lanthanide ions has allowed antibody labeling with detection sensitivities similar to those obtainable with radioisotopes. Use of europium and terbium chelators for time-resolved fluorometric assays is described in U.S. Pat. No. 5,854,008, the contents of which are hereby incorporated by reference. In a preferred embodiment, an antibody-$Eu^{+3}$ conjugate is formed in accordance with manufacturer's instructions. Approximately 100 µl of labeled antibody is added to each well and the plate is permitted to incubate with shaking for a period of time sufficient to allow binding of the antibody to the phosphorylated protein bound to the plate. The plate is then washed to remove unbound antibody. Enhancement Solution for measuring $Eu^{3+}$ (E. G. & G. Wallac, Turku, FI) is added and the amount of labeled antibody bound is measured using a time-resolved fluorescence plate reader (Wallac Oy, Turku, FI).

Screening Test Compounds

The method of the present invention can be used to test for compounds that modulate tyrosine kinase activity and which act as tyrosine kinase receptor function agonists or antagonists. In one embodiment, cells bearing the receptor of interest are exposed to known agonists, known antagonists, and/or test compounds which may be, or may contain, agonists or antagonists. An agonist, antagonist, or test compound may be a chemical compound, a mixture of chemical compounds, a biological macromolecule, or an extract made from biological materials such as bacteria, plants, fungi, or animal cells or tissues. Test compounds are evaluated for potential activity as agonists or antagonists of receptor activation by inclusion in screening assays described herein. An "agonist" enhances the activity of a receptor; an "antagonist" diminishes the activity of a receptor. The terms "agonist" and "antagonist", as used herein, do not imply a particular mechanism of function.

In accordance with the method of the present invention, cells are incubated with a known agonist, a test compound, or a combination of the two for a period of time in the range of 1 minute to several hours and a range of temperature from about 4° C. to about 37° C. In a preferred embodiment, the cells are incubated in the presence of test compound and ligand/activator for 15 minutes at room temperature. The cells are then lysed and a sample of the cell lysate assayed in a capture assay plate as described above.

In a preferred embodiment, the resulting cell lysate is transferred to a well of a microtiter plate to which an antibody against the phosphorylated proteins is immobilized. In an alternative embodiment, a cell membrane fraction, especially a plasma membrane fraction can be purified from the cells treated with a test compound, using standard methods (Methods in Enzymology Vol. 198) and assayed for tyrosine kinase activity in accordance with the method of the subject invention.

Time Resolved Fluorescence

In one embodiment, the detection method employed for determining the level of anti-phosphotyrosine detecting antibody is time-resolved fluorescence (TRF). Lanthanide-ion-chelates possess unique fluorescent properties, making them particularly good reporter groups for high-throughput applications. For this method, anti-phosphotyrosine antibodies may be labelled with europium (Eu), terbium (Tb), dysprosium (Dy) or samarium (Sm), with europium and terbium being preferred and europium being most preferred. In a preferred embodiment, anti-phosphotyrosine antibodies, for example, pY99 (available from Santa Cruz Biotech, Inc., Santa Cruz, Calif.; Upstate Biotechnology, Inc., Lake Placid, N.Y.; or Transduction Laboratories,) are labeled with a lanthanide ion, such as Europium ($Eu^{3+}$) according to manufacturer's instructions. Briefly, anti-phosphotyrosine antibody (1 mg) is dialyzed against 50 mM sodium bicarbonate pH 8.35, 0.9% NaCl and adjusted to a concentration of 2 mg/ml. 0.5 ml of the antibody solution is mixed with 300 nmol Europium-DTTA labeling reagent (E. G.& G. Wallac, Inc., Turku, FI) in bicarbonate buffer (50 mM Sodium Bicarbonate, 150 mM NaCl, pH 8.0) and the reaction mixture is incubated at 16° C. overnight in the dark. $Eu^{3+}$-chelate-labeled antibody is then separated from free $Eu^{3+}$-chelate by gel-filtration chromatography on an S200 FPLC column (Pharmacia, Bridgewater, N.J.).

EXAMPLE 1

The following example(s) describes the application of the assay of the invention using cells expressing T-cell receptor (T-cells) or IgM (B-cells).

According to the method of the present invention, cells of interest were grown under conditions appropriate for growth, proliferation and for expression of the receptor of interest according to methods of cell culture known to one of ordinary skill in the art.

96-well polystyrene plates were coated with an anti-phosphotyrosine antibody, pY99 (Santa Cruz Biotech, Inc., Santa Cruz, Calif.), by adding 200 μl of an antibody solution in Tris buffered saline (TBS) pH 8.0 at a concentration of 2.5 μg/ml. The plates were incubated for three hours at room temperature. The plates were then rinsed and 300 μl of blocking solution, sold under the trademark, SUIPER-BLOCK® (Pierce Chemical, Rockford, Ill.) was added and the plates were incubated for two hours. At this point, the plates may be stored at 4° C. for up to two weeks.

50 μl of a cell suspension containing human or animal cells of interest, for example, Jurkat T cells, Ramos B cells, or Daudi B cells, at a cell density of $2-5\times10^5$, were added to each well of a 96-well polypropylene U-bottom plate. 10 μl of test compound in a physiologic buffer was added to the cells to a final concentration in the range of 1–10 μM. Control wells received 10 μl of buffer with no test compound. The appropriate ligand or activator for the receptor of interest, for example, anti-CD3 antibody to activate the T-cell receptor, or anti-IgM to activate the B-cells via cell surface immunoglobulin, was added in 10 μl, so that the final concentration of ligand was 100 ng/ml; the plate was incubated for 15 minutes. The cells were then lysed with 50 μl of standard detergent buffer containing phosphatase inhibitors (10% triton X-100, 50 mM sodium fluoride, 2 mM EDTA, 2 mM EGTA). The plate was frozen at −80° C. and may be stored indefinitely.

To assay the cell lysates for kinase activity, the plate was thawed at 37° C., and 100 μl of tris buffered saline with 0.1% Tween 20 was added to each well. After shaking the plate for 15 minutes, 180 μl of the cell lysate from each well was transferred to the capture plate described above. The capture plate was incubated for one hour at room temperature with shaking to allow the phosphorylated proteins contained in the cell lysate to bind to the antibody coated plate. The plate was then washed to remove unbound protein. Relative phosphorylated protein levels were detected by adding 100 μl of a 0.2 μg/ml solution of europium-chelate labeled anti-phosphotyrosine antibody in tris buffered saline (pH 8.0) to each well and allowing the plate to incubate for one hour with shaking. The plate was then washed to remove unbound antibody. Enhancement Solution for measuring $Eu^{3+}$ (E. G. & G. Wallac, Turku, FI) was added and the amount of labeled antibody bound was measured using a time-resolved fluorescence plate reader, for example, a Wallac 1420, or Victor MLC (Wallac Oy, Turku, FI).

Figure 1:
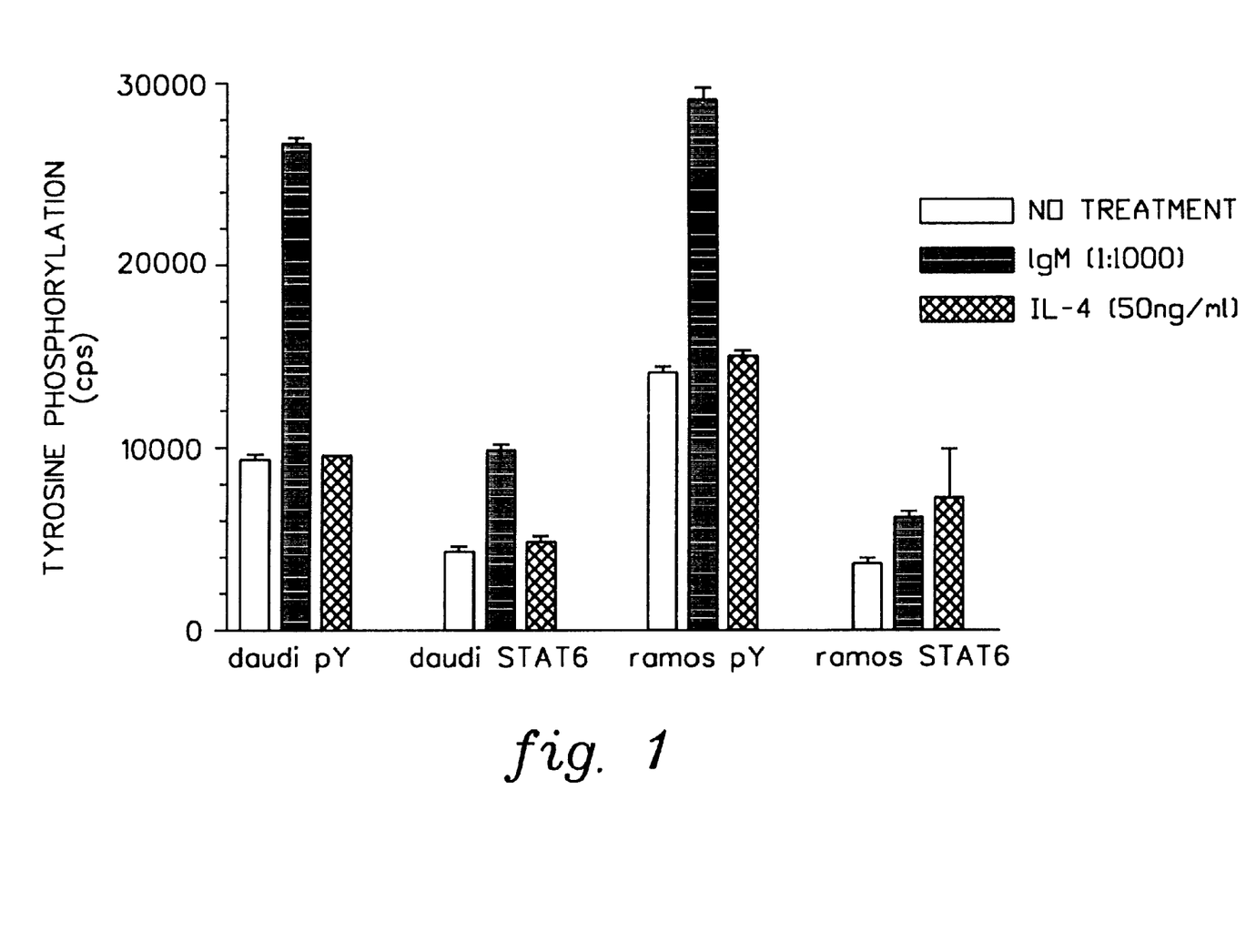
FIG. 1 shows the changes in tyrosine phosphorylation as detected by the method of the present invention when B-cells are stimulated with anti-IgM.

The results, as shown in FIG. 1, indicate that changes in tyrosine phosphorylation can be detected by stimulating Daudi or Ramos B-cells with anti-IgM but not significantly with IL-4. It is known that an anti-IgM antibody, which stimulates the B-cell receptor, results in detectable changes in phosphorylation of many proteins.

EXAMPLE 2

Figure 2:
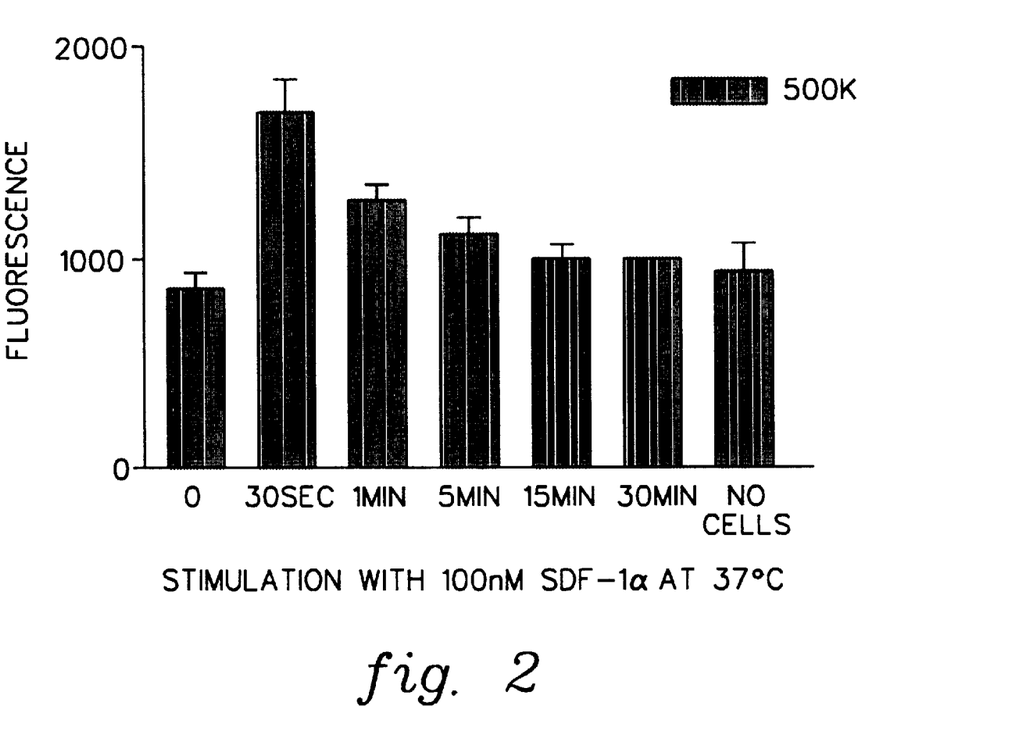
FIG. 2 shows the results of stimulating Jurkat cells with SDF-1α for various lengths of time prior to assaying for tyrosine kinase activity in accordance with the method of the invention.

In this example, Jurkat cells were incubated at 37° C. with 100 nM SDF-1α for various time intervals prior to harvesting of the cells and measurement of tyrosine kinase activity. The results are shown in FIG. 2. There is a decrease in kinase activity (as indicated by a decrease in fluorescence) as time increases suggesting an intracellular dephosphorylation event following cell activation by SDF-1α.

Confocal Microscopy

In one embodiment of the present invention, measurement of the amount of bound and free signal in the assay is accomplished through the use of microscopy. This can be carried out, for example, by sequentially viewing different depths in the sample using a conventional microscope employing a narrow depth of focus. According to a preferred method of the invention, however, confocal microscopy is employed, for example, as described in U.S. Pat. No. 5,876,946, the contents of which are incorporated by reference herein, to determine the amount of signal bound to a solid support, for example, individual cell sized particles.

Confocal microscopy confines detection of an illuminated object, or sample, to a thin object plane. A view of a "slice" of the object, or sample, is obtained. This is achieved, for example, by placing a spatial filter, such as a pinhole, in the image plane located between the objective lens and a detector. Only light emitted from a narrow region near the object plane converges through the spacial filter. Light from other planes is blocked by the filter. Images are obtained of the object plane, e.g., by scanning, in sequence, the points in the field of view, to obtain the "slice".

Confocal microscopy using laser scanning is particularly preferred for use in the invention. A suitable laser scanning microscope is sold as "IMAGN/2000" by Biometric Imaging Inc. (Mountain View, Calif.). Laser scanning microscopes are also described in U.S. Pat. Nos. 5,556,764 and 5,547,849. These microscopes are conventionally used to analyze blood within a capillary tube to determine the number of cells labelled by fluorescent antibodies.

Non-laser scanning confocal microscopes are well known and can also be used to practice the invention. For example, confocal microscopes using spinning Nipkow disks, or similar arrangements can be used, if desired. Such microscopes are described, e.g., in Dixon (1996) *Nature*, 383:760; Juskaitis et al. (1996) *Nature* 383:804; Petran et al. (1968) *J Opt. Soc. Am.* 58, 661; and Xiao et al. (1988) *Appl Phys. Lett.* 53:716.

Useful confocal microscopes are also described, for example, in U.S. Pat. Nos. 5,032,720; 5,120,953; 5,260,578; 5,304,810; 5,283,684; 5,351,152, and 5,162,946.

According to the method of the invention, data obtained by confocal microscopy are analyzed to determine the difference between signal associated with individual suspended cells or solid supports, and background signal, and to obtain a measure of bound versus unbound antibody. The use of confocal microscopy as the detection method for the assay of the present invention obviates the need to remove unbound signal. Conventional confocal microscopy for, e.g., counting CD4+ cells, is not concerned with this determination, or with high throughput screening of compounds.

When using confocal microscopy as the detection method, any desired optically detectable label can be used, including fluorescent labels and chemiluminescent labels. If the label is chemiluminescent, it is preferred that it generate a short-lived signal. Enzymes that produce a visible color change in the presence of appropriate substrate, such as horse radish peroxidase and alkaline phosphatase, can also be used. Fluorescent labels are preferred and are described below with respect to preferred embodiments of the invention. Other photometrically detectable labels, however, may be substituted in these embodiments if desired.

In one embodiment, the assay screens compounds for their ability to modulate kinase activity in a biological sample. Capture assay plates, or alternatively suspendable solid supports, such as beads, are prepared as described above. A portion of a biological sample is exposed to a test compound, and the sample is then added to capture assay plates or beads. Differences in binding of fluorescently labeled antibody between treated and untreated portions reflect the modulatory effect of the test compound on the kinase activity in the sample. The degree of antibody binding is determined by measuring, through confocal microscopy, amounts of labeled antibody bound to phosphorylated molecules captured on individual supports.

In addition to screening test compounds for their ability to modulate kinase activity in a biological sample, the method of the invention is also useful in examining the rate at which the modulation occurs. For example, cells may be incubated in the presence and absence of a test compound as described above, for different time intervals (e.g. 5 mins., 10 mins., 15 mins., . . . 1 hour, 2 hours and so on) prior to lysing and assay in the capture assay.

A suspension of antibody-coated beads can be contacted with a biological sample, for example, a cell lysate from cells incubated in the presence and absence of test compounds to be screened for their ability to modulate tyrosine kinase activity. As an example, a library of compounds to be screened for inhibition of tyrosine kinase activity is contacted with a suspension of cells. The cells are subsequently lysed and assayed as described above. The anti-phosphotyrosine antibody-coated beads capture the phosphorylated proteins in the cell lysate and can then be detected with a second labeled anti-phosphotyrosine antibody. When examined by confocal microscopy, capture beads bound by labeled anti-phosphotyrosine antibodies appear as regions of increased fluorescence on a background of relatively constant "free" label. The amount of bead-associated fluorescence is less in an assay where active compound inhibits tyrosine kinase activity.

Basically, in a confocal microscopic image, cells or beads that are significantly more fluorescent than the background show up as more intense spots. Presence of a "spot" relative to background fluorescence indicates bound antibody, while the background fluorescence itself results from free antibody. Confocal microscopy allows measurement of individual cell or bead-sized "spots" of bound fluorescence. The amount of free fluorescent antibody can be simultaneously determined.

In the assay of the invention, the amount of fluorescence associated with individual solid supports in the assay is totaled. This total provides a measure of the amount of antibody bound to phosphorylated molecules. This amount is compared to the amount of free fluorescence to arrive at a value indicative of the amount of kinase activity in the biological sample. Specific methodologies for arriving at particular values indicating binding are described below. While background fluorescence can be individually measured in each assay, this may not be necessary where the background fluorescence is relatively constant.

The method of the invention is particularly advantageous in increasing the ratio of signal to background noise. By eliminating signal from label contained in solution outside of the "slice" containing the measured particles or cells, the background noise is significantly reduced. The ratio of signal to background noise was found to be about fifteen times lower in a commercially available conventional heterogeneous (i.e., separation-based) assay using $^{125}$I labeled ligand than in the method of the invention.

The method is especially effective in measuring fluorescence for samples that have been allowed to settle. In one embodiment, magnetic beads are employed as the solid support and the beads are caused to settle by application of a magnetic force upon the beads. Confocal microscopy allows accurate measurement of a "slice" or "section" of liquid in a container. Thus, measurement can be taken of, e.g., the bottom 10% of the sample where fluorescence bound to the solid particles is concentrated. This is not possible in prior art assays using conventional optical detection since such assays do not eliminate signal from the volume above the settled cells or solid particles. Elimination of this signal accounts, in part, for the very high signal to noise ratio achieved by the method of the invention.

Preferably, the suspended solid supports are allowed or caused to settle for about 10 minutes or more, so that more than about 75% of the supports are contained in less than about 25% of the volume of the assay container, i.e., solid support layer forms on the bottom. Most preferably, more than 90% of the cells or supports are allowed to settle in less than about 10% of the volume of the container. In one preferred embodiment, the thickness of the layer of cells or supports is about the same as the thickness of the confocal object plane. The time required for settling is partly a function of column height, and so is higher, e.g., for samples in 96 well plates than for samples in 1536 well plates.

Preferably, the assay of the invention is performed using a microtiter plate having microvolume containers, such as the 1536 well plate described in U.S. patent application Ser.

No. 60/037,636 filed Feb. 18, 1997. A confocal scanning microscope sequentially scans the bottom of each well in the microtiter plate.

The method can also be carried out in conventional 96 well microtiter plates, or in any other container or on any surface capable of holding liquid samples and of being scanned by a confocal microscope. Examples include 12-well, 24-well, 384-well, 864-well plates, and microscope-slides.

In one embodiment of the invention, in which suspendable supports are employed in the preferred size of about 6 $\mu$m, the desired density of suspendable supports will preferably be between about 100 and 1000 cells per microliter in a 1536 well plate and between about 30 to 300 cells per microliter in a conventional 96 well plate. The density varies depending on the size of the supports and the amount of antibody affixed to each support. Typically, it is believed necessary to measure signals from at least 5 to 1000 supports per sample to obtain a statistically relevant result. The optimum density can be determined using these concentrations as a guideline, as well as the size of the particular cells employed, and by measuring the signal provided in assays using known modulators of the kinase activity. The area scanned can be limited to reduce scanning time and thereby increase throughput, as long as the number of supports measured is sufficient.

The signal detected according to the invention, is preferably generated by a fluorescent label. Fluorescent labels suitable for use in the invention are well known and include cyanine dyes such as Cy-5, Cy-5.5, and Cy7 (Amersham Corp.), fluorescein, rhodamine and Texas red. In a preferred embodiment, anti-phosphotyrosine antibodies, for example, pY99 (available from Santa Cruz Biotech, Inc., Santa Cruz, Calif.; Upstate Biotechnology, Inc., Lake Placid, N.Y.; or Transduction Laboratories,) are labeled with monofunctional Cy5 dye according to manufacturer's (Amersham) instructions. In one embodiment of the invention, it is preferred that the fluorescent label fluoresce at a relatively high wavelength, i.e., higher than about 450 nm, to avoid interference from cell originating fluorescence and fluorescence originating from glass and plastic containers. The labels most preferably fluoresce above 600 nm, and at less than about 800 nm. Labels that excite at about 400–800 nm can avoid photobleaching caused by near-UV light. A preferred excitation wavelength is about 633 nm.

In a separate embodiment of the invention, the assay is performed to determine the degree of binding to a treated surface of an insuspendable solid support. The support can be a container, or vessel, itself, such as the bottom of a microtiter plate. Alternately, the insuspendable support can be, e.g., a disc. In the embodiment in which the support is the bottom of the well of the microtiter plate, the plate is coated with the capture antibody, contacted with the biological sample containing the kinase activity to be measured and then exposed to labelled antibody, as described above. A confocal section including the bottom of the plate is measured for optically detectable signal. Free signal is measured in other confocal sections that do not include the bottom of a microtiter plate. The signal bound to the support can then be calculated. This method is advantageous in that scanning can be rapidly performed. Individual beads do not need to be identified, resulting in higher throughput. Use of a thin confocal object plane is preferred to exclude signal emanating from above the coated plate, and to maintain a high signal to noise ratio. In one embodiment of this method, the thickness of the confocal object plane is less than about 10 $\mu$m.

Data Analysis

The data that results from the IMAGN system consists of a tab delimited text file that contains information about each particle that has been identified in the field. The IMAGN system provides position, shape, and intensity data (for two channels, Cy5 and Cy5.5) for each particle in the imaging field, as well as baseline information. (In a typical analysis using this type of equipment, particles are identified by two or more contiguous pixels having intensities significantly greater than the baseline signal.) Statistical parameters (e.g., standard deviations) of the data are also tabulated. This data can be analyzed to give a scalar value for the sample which provides a measure of the amount of antibody binding. Three possible ways to perform this further analysis are described below.

(a) Mean Fluorescence Intensity. This value is derived from the data table as the mean value across all particles of "MaMO". Channel 0 (zero) is the Cy5 fluorescence channel, and the MaMO value is calculated as the peak Cy5 fluorescence (corresponding to fluorescence bound to the particle) with the minimum (baseline fluorescence) value subtracted out. "MaMO" is tabulated for each particle in the field.

This analysis is particularly useful for assays that involve high fluor concentrations and relatively high levels of bound antibody as the result of high levels of kinase activity. It may not be advantageous where all particles cannot be detected, e.g., at low fluor concentrations or low levels of antibody binding. Analysis of F value (explained below) can provide more accurate data under these circumstances. The F-value measures the total fluorescence in the particle layer and therefore provides a more accurate measurement when all particles cannot be counted.

(b) F-value. The F-value is determined by multiplying the MFI by the total number of particles loaded into the well (as opposed to the number of fluorescent particles counted), and dividing by 1000. This value provides the total fluorescence of the particle layer, and includes particles whose fluorescence is so weak as to be undetectable in a given scan by the confocal microscope. The F-value is believed to generally provide a more accurate measure of binding in a given sample.

(c) Percent of Control. Percent of control analysis can be performed using values obtained from either an MFI or F-value analysis, and results in normalization of this data. It is calculated according to the following formula for the relevant value. "Max" and "min" refer to the maximum and minimum fluorescence for the relevant value.

$$\% \text{ Control} = ((\text{Value} - \text{Min})/(\text{Max} - \text{Min})) \times 100$$

Detection of labeled antibody by confocal microscopy makes the method of the present invention particularly well-suited for high-throughput screening. The variability in the results is low and the results strongly correlate with those obtained by conventional methods of analysis. The method is easily performed in a microscopic volume. It is, therefore, well-suited for high-throughput screening in microliter samples, such as when using a 1536-well plate, and allows efficient use of small quantities of reagents.

What is claimed is:

1. A method for screening a substance for the ability to modulate tyrosine kinase activity comprising the steps:

(a) exposing a portion of a biological sample to said substance;

(b) determining the level of tyrosine kinase activity in said exposed portion and in an unexposed portion by:

(1) contacting said portions individually with a solid phase coated with a first anti-phosphotyrosine antibody so that phosphorylated tyrosine-containing molecules in the biological sample are bound by the antibody to the solid phase;

(2) contacting the phosphorylated tyrosine-containing molecules that are bound by the first anti-phosphotyrosine antibody to the solid phase with a second labeled anti-phosphotyrosine antibody; and (3) measuring the amount of labeled anti-phosphotyrosine antibody bound to the solid phase, wherein the amount of labeled anti-phosphotyrosine antibody indicates the level of tyrosine kinase activity in the portions; and (c) comparing the level of tyrosine kinase activity in said exposed portion with the level of tyrosine kinase activity in the unexposed portion, wherein a difference between the levels indicates that the substance has the ability to modulate tyrosine kinase activity.

2. The method of claim 1, further comprising the step of comparing the level of tyrosine kinase activity in the exposed and unexposed portions of said biological sample with a standard having a known level of tyrosine kinase activity.

3. The method of claim 1, wherein said biological sample is a cell fraction.

4. A method for screening a substance for the ability to modulate tyrosine kinase activity comprising the steps:

(a) exposing a portion of a cell population to said substance;

(b) preparing cell fractions from cells of said exposed portion and from an unexposed portion of said cell population; and (c) determining the level of tyrosine kinase activity in said cell fractions by:

(1) contacting said cell fractions with a solid phase coated with a first anti-phosphotyrosine antibody so that phosphorylated tyrosine-containing molecules in the cell fractions are bound by the antibody to the solid phase;

(2) contacting the phosphorylated tyrosine-containing molecules bound by the first anti-phosphotyrosine antibody to the solid phase with a second labeled anti-phosphotyrosine antibody and (3) measuring the amount of labeled anti-phosphotyrosine antibody associated with the solid phase; and (d) comparing the level of tyrosine kinase activity in said exposed portion with the level of tyrosine kinase activity in the unexposed portion.

5. The method of claim 4 wherein portions of a cell population are exposed to the test compound for different lengths of time.

6. The method of claim 4, further comprising the step of comparing the level of tyrosine kinase activity in said cell fractions with a standard having a known level of tyrosine kinase activity.

7. The method of claim 1, wherein said first and second anti-phosphotyrosine antibodies are the same.

8. The method of claim 1, wherein the label on said labeled anti-phosphotyrosine antibody is selected from the group consisting of Cy5, Cy5.5, Cy7 and a lanthanide ion.

9. The method of claim 1, wherein said lanthanide ion is europium.

* * * * *

UNITED STATES PATENT AND TRADEMARK OFFICE
CERTIFICATE OF CORRECTION

PATENT NO. : 6,806,056 B2
DATED : October 19, 2004
INVENTOR(S) : Glickman et al.

It is certified that error appears in the above-identified patent and that said Letters Patent is hereby corrected as shown below:

Column 7,
Lines 55 and 56, delete the word "SUIPER-BLOCK®" and insert -- SUPER-BLOCK® --

Signed and Sealed this

Twenty-first Day of December, 2004

JON W. DUDAS
*Director of the United States Patent and Trademark Office*

UNITED STATES PATENT AND TRADEMARK OFFICE
CERTIFICATE OF CORRECTION

PATENT NO. : 6,806,056 B2
DATED : October 19, 2004
INVENTOR(S) : Glickman et al.

It is certified that error appears in the above-identified patent and that said Letters Patent is hereby corrected as shown below:

Column 5,
Line 67, insert -- 10% -- after the word "example,"

Signed and Sealed this

Twelfth Day of April, 2005

JON W. DUDAS
*Director of the United States Patent and Trademark Office*